United States Patent
Bishop et al.

(10) Patent No.: US 9,823,894 B2
(45) Date of Patent: Nov. 21, 2017

(54) CONTROLLING AUDIO TEMPO BASED ON A TARGET HEART RATE

(71) Applicant: International Business Machines Coporation, Armonk, NY (US)

(72) Inventors: Adam T. Bishop, Roanoke, VA (US); Matthew R. Catalfamo, Clay, NY (US); Al Chakra, Apex, NC (US); Indrajit Viswanath, Atlanta, GA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/824,288

(22) Filed: Aug. 12, 2015

(65) Prior Publication Data

US 2017/0046119 A1 Feb. 16, 2017

(51) Int. Cl.
  *G06F 17/00* (2006.01)
  *G06F 3/16* (2006.01)
  *G05B 15/02* (2006.01)
  *A61B 5/11* (2006.01)

(52) U.S. Cl.
  CPC .............. *G06F 3/165* (2013.01); *A61B 5/11* (2013.01); *G05B 15/02* (2013.01); *G10H 2210/391* (2013.01); *G10H 2220/201* (2013.01)

(58) Field of Classification Search
  CPC ............ A63B 71/0686; A63B 2230/06; A63B 2024/0068; A63B 22/00; A63B 71/0622; G10H 2210/391; G10H 2220/201; G06F 17/30764
  See application file for complete search history.

(56) References Cited

U.S. PATENT DOCUMENTS

| 8,267,942 | B2 | 9/2012 | Szabo et al. | |
|---|---|---|---|---|
| 8,808,144 | B2 | 8/2014 | Ogg et al. | |
| 2007/0169614 | A1* | 7/2007 | Sasaki | A63B 69/0028 84/612 |
| 2008/0097633 | A1 | 4/2008 | Jochelson et al. | |
| 2008/0153671 | A1* | 6/2008 | Ogg | A63B 71/0686 482/3 |
| 2015/0181314 | A1* | 6/2015 | Swanson | H04Q 9/00 340/870.07 |

* cited by examiner

*Primary Examiner* — Thomas Maung
(74) *Attorney, Agent, or Firm* — Cantor Colburn LLP

(57) ABSTRACT

A method for controlling an audio output comprises playing a first audio file having a first tempo, measuring a first heart rate of a user, determining whether the first heart rate of the user is greater than a target heart rate, and playing a second audio file having a second tempo, the second tempo is slower than the first tempo, responsive to determining that the first heart rate of the user is greater than the target heart rate.

12 Claims, 9 Drawing Sheets

US 9,823,894 B2

CONTROLLING AUDIO TEMPO BASED ON A TARGET HEART RATE

BACKGROUND

The present invention relates to fitness devices, and more specifically, to audio that matches a desired cadence and heart rate. Athletes often train using a heart rate monitor that outputs the heart rate of the athlete. The athlete often aims to achieve and maintain a target heart rate. Training at the target heart rate often improves the fitness gains of the athlete and improves the efficiency of their training.

SUMMARY

According to an embodiment of the present invention, a method for controlling an audio output comprises playing a first audio file having a first tempo, measuring a first heart rate of a user, determining whether the first heart rate of the user is greater than a target heart rate, and playing a second audio file having a second tempo, the second tempo is slower than the first tempo, responsive to determining that the first heart rate of the user is greater than the target heart rate.

According to another embodiment of the present invention, a computer program product for outputting audio, the computer program product comprising a computer readable storage medium having program instructions embodied therewith, the program instructions executable by a processor to cause the processor to perform a method that comprises playing a first audio file having a first tempo, measuring a first heart rate of a user, determining whether the first heart rate of the user is greater than a target heart rate, and playing a second audio file having a second tempo, the second tempo is slower than the first tempo, responsive to determining that the first heart rate of the user is greater than the target heart rate.

According to yet another embodiment of the present invention, a system for outputting audio comprises a processor operative to play a first audio file having a first tempo, measure a first heart rate of a user, determine whether the first heart rate of the user is greater than a target heart rate, and play a second audio file having a second tempo, the second tempo slower than the first tempo, responsive to determining that the first heart rate of the user is greater than the target heart rate.

DETAILED DESCRIPTION

Figure 1:
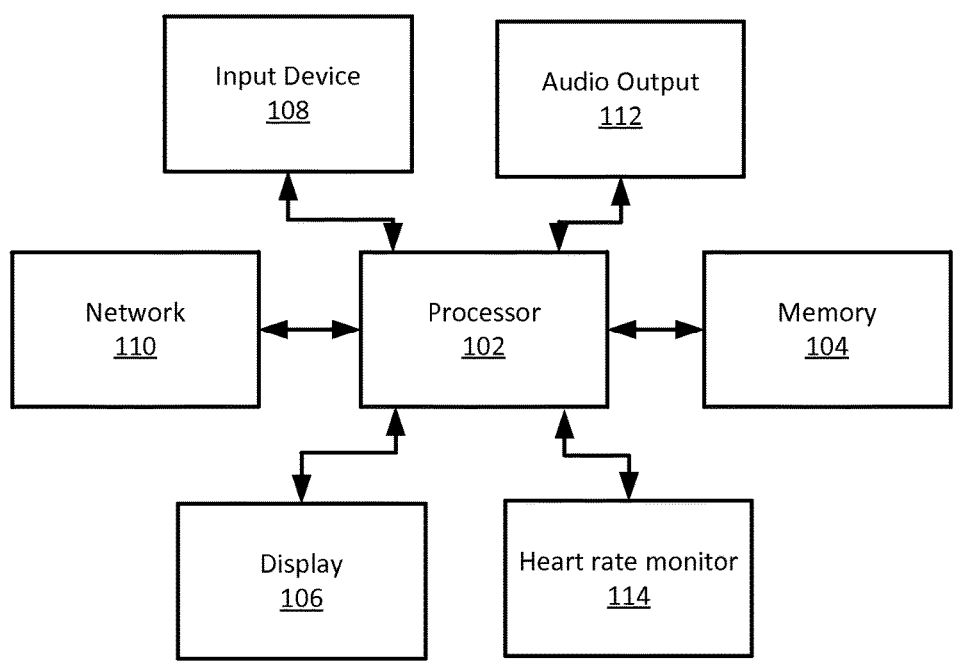
FIG. 1 illustrates a block diagram of an exemplary system for controlling audio based on a target heart rate.

FIG. 1 illustrates a block diagram of an exemplary embodiment of a system 100 that includes a processor 102 that is communicatively connected to a memory 104, a display 106, an input device 108, a network 110, an audio output 112, and a heart rate monitor 114. The audio output 112 may include a speaker system, headphones, or a wireless connection to audio output devices such as wireless speakers or headphones. The heart rate monitor 114 may include any device that is operative to measure and output a heart rate of a user. The system 100 may include, for example, any mobile processing device such as, a mobile audio player, smart phone, heart monitor, or other computer systems. The processor 102 may communicatively connect with other processors or servers via the network 110, which may perform some of the functions described herein in some exemplary embodiments.

Athletes often use a heart rate monitor to monitor their heart rates while they are exercising. Athletes often set a target heart rate that they would like to achieve and maintain during their workout. In some workouts the athlete sets a warmup heart rate or heart rates that they would like to achieve during a warmup period. In many cardiovascular workouts such as, running, walking, or using cardiovascular exercise machines, athletes listen to music. The music has a cadence or tempo, and the athlete often matches the pace of their exercise with the cadence of the music. Since different songs usually have different cadences, it is desirable to match the cadence of a song with a desired exercise pace. The pace and duration of the exercise often corresponds to the heart rate of the athlete. Thus, the cadence of a song may be used to help an athlete set a pace that corresponds to a desired heart rate. Typically, a song with a faster cadence results in an athlete having a faster pace and faster heart rate, while a song with a slow cadence results in a slower pace and a slower heart rate.

The embodiments described below provide a method and system for changing the cadence of an audio output based on a measured heart rate of a user and a desired heart rate of a user during a workout.

FIGS. 2A-2H, illustrate a flow diagram that includes a method for controlling the output of an audio device based on a measured heart rate of a user and a desired heart rate. The output of the audio device may include any audio including for example, music, spoken words, tones, or any other type of audio output.

Figure 2A:
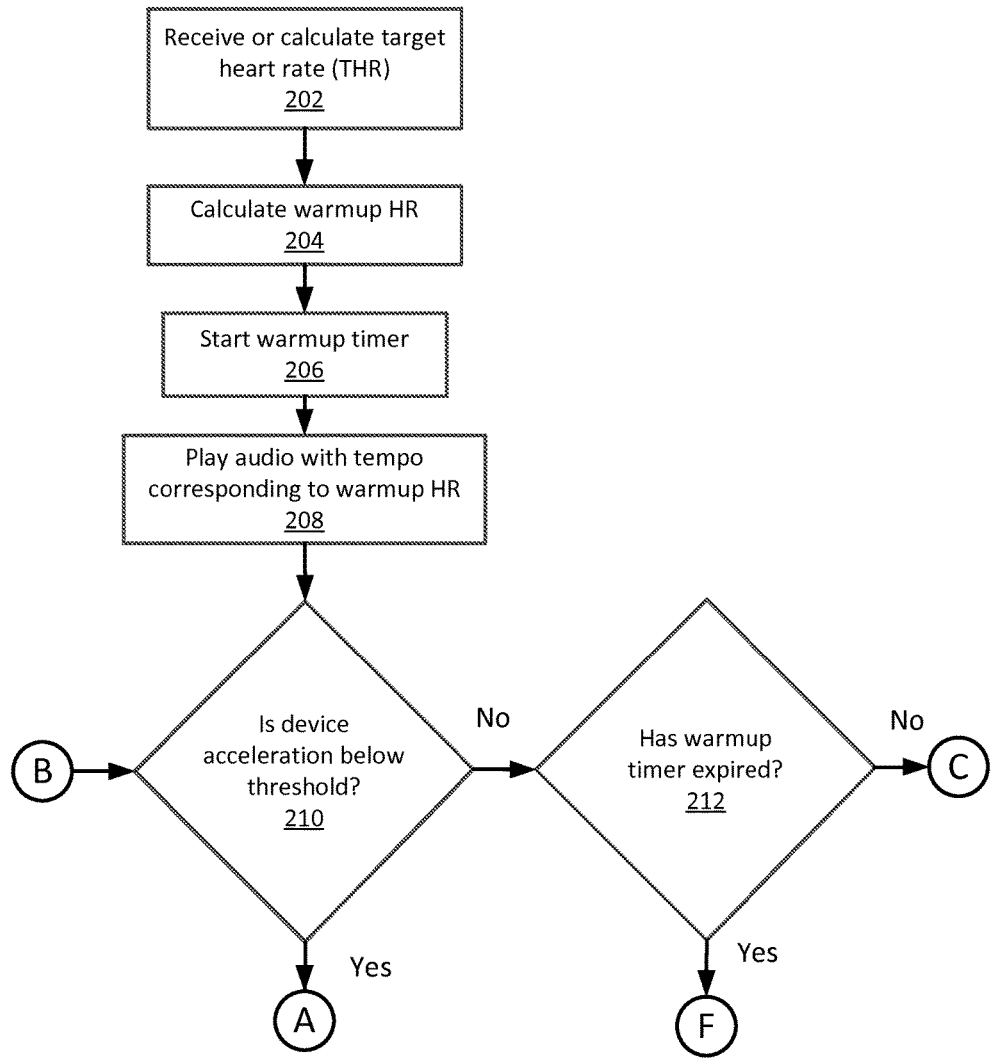
FIGS. 2A-2H illustrate a block diagram of an exemplary method for operating the system of FIG. 1.

Referring to FIG. 2A, in block 202 the system 100 (of FIG. 1) receives or calculates a target heart rate (THR). The target heart rate is the desired heart rate that the user would like to achieve and maintain during their workout. In the illustrated embodiment, the user may enter a target heart rate, or the system 100 may generate a target heart rate based on any number of factors such as, for example, the weight, age, gender, and fitness level of the user. Alternatively, the target heart rate may be generated based on data collected from previous workouts that the user has performed.

Often a workout may be divided into phases such as a warmup phase, workout phase, and cool down phase. The target heart rate during the warmup phase may be lower than the target heart rate during the workout phase. Thus, in block 204, a warmup heart rate may be calculated. The warmup heart rate may be calculated by, for example, reducing the target heart rate by a default or user entered percentage. In alternate embodiments, the user may enter the warmup heart rate, or may set the warmup heart rate to be the same as the target heart rate if desired.

In block 206 the warmup timer starts. The warmup timer may run for a default period of time, or may be set by the user. The warmup timer runs during the warmup phase of the workout.

In block 208, audio that has a tempo that corresponds to the warmup heart rate is output from the system 100 (of FIG. 1) via the audio output 112. In this regard, the audio may include any audio with a beat, cadence, tempo, or other periodic sound such as tones, music, or spoken words. The memory 104 of the system 100 may include, for example, a library of audio files having different tempos. The system 100 may, in some embodiments, analyze the library of audio files to determine the tempo of each of the audio files and save the determined tempo as metadata associated with each audio file. Alternatively, the audio files may be input into the memory of the system 100 with metadata that indicates the tempo of the audio files. The system 100 may, in some embodiments, change the tempo of the output audio files such that the tempo of an output audio file may be dynamically adjusted by the system 100 during playback to increase or decrease the tempo of the output audio.

In block 210, the system 100 determines whether the acceleration of the system 100 is below a threshold value. The acceleration of the system 100 may be determined using, for example, an accelerometer or global positioning system input from the input device 108. If the acceleration of the system 100 is below the threshold level, the system assumes that the user is not actively working out. If the acceleration of the system 210 is below the threshold in block 210, the system 100 pauses the audio output in block 214 (of FIG. 2B).

Figure 2B:
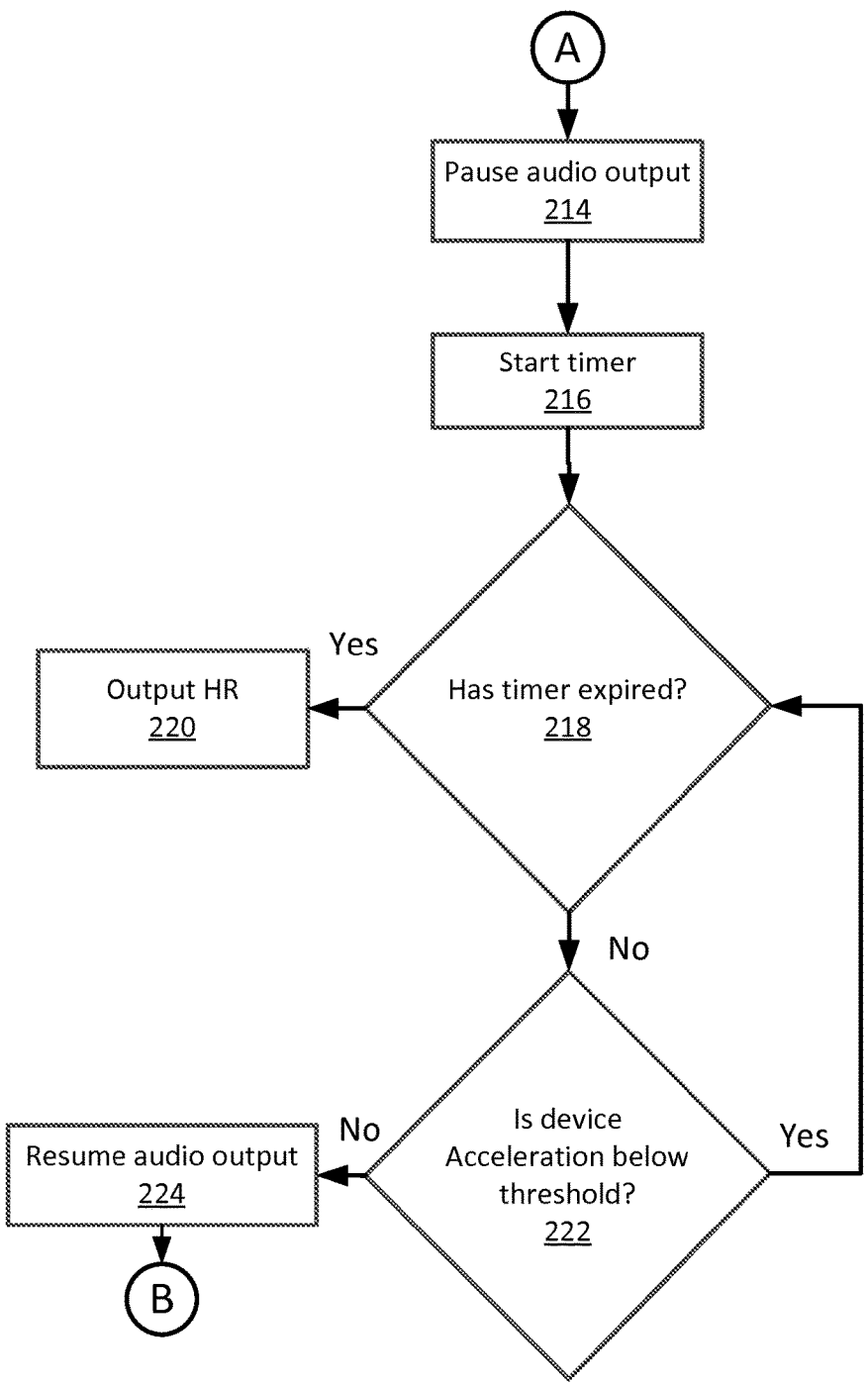

Referring to FIG. 2B, in block 216, the system 201 starts a timer after the audio output is paused. In block 218, the system 100 determines whether the timer has expired. If yes, the heart rate is output to the user on the display 106 (of FIG. 1) in block 220. If the timer has not expired in block 218, the system 100 determines whether the acceleration of the system 100 is below the threshold level. If no, the system 100 resumes the audio output in block 224. By starting the timer in block 216 after the acceleration has been determined to be below the threshold, the system 100 may pause audio output for the period of the timer while the user has stopped working out. If the user resumes moving or working out prior to the expiration of the timer, the audio resumes playing.

Figure 2C:
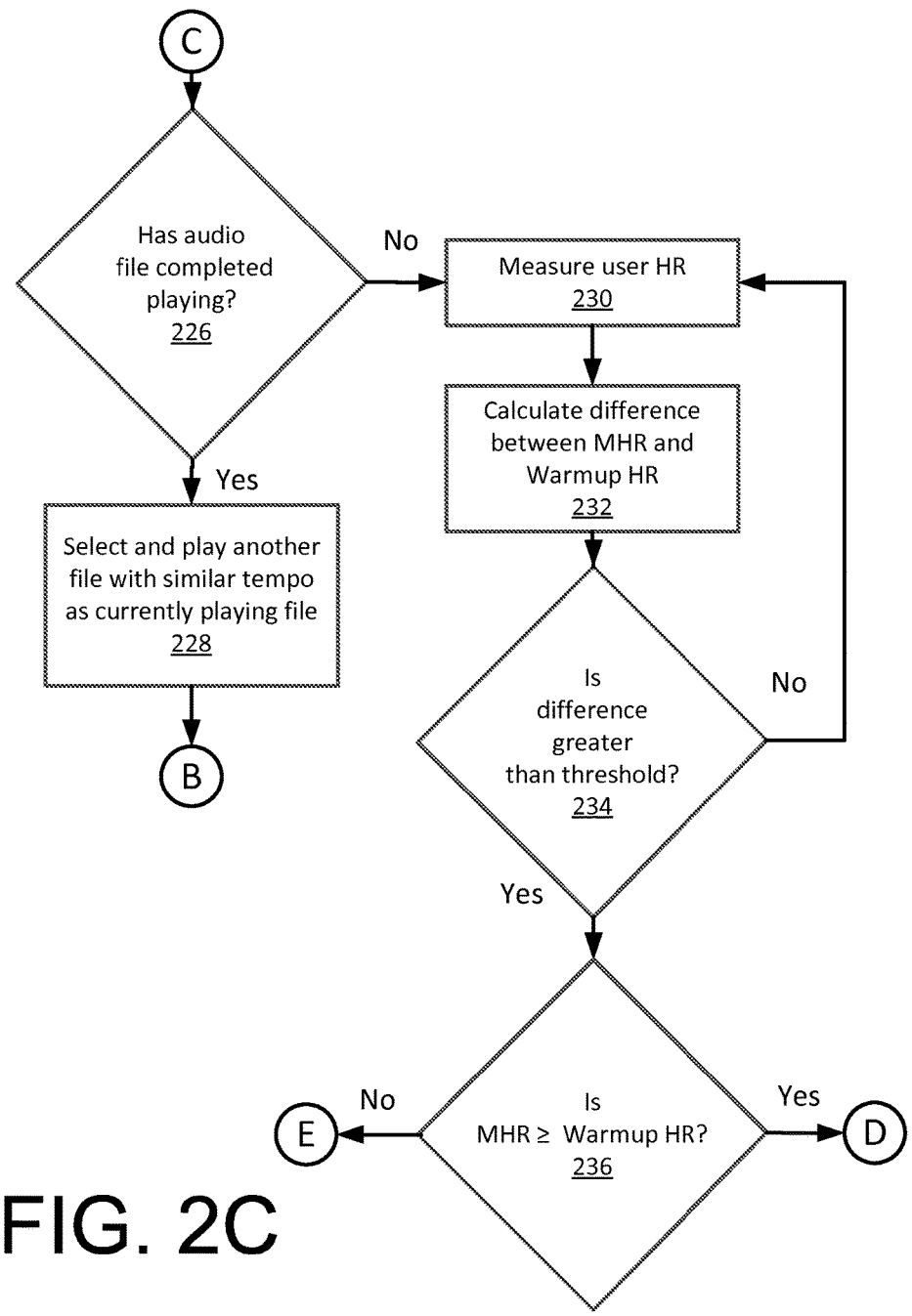

Referring to FIG. 2A, if the acceleration of the device is not below the threshold in block 210 (i.e., the system 100 is moving indicating that the user is working out) the system 100 determines whether the warmup timer has expired in block 212. If no, the system 100 determines whether the audio file has completed playing in block 226 (of FIG. 2C). If yes, in block 228, the system 100 selects and plays another audio file with a similar tempo as the tempo of the previously playing audio file. Referring to FIG. 2C, if the audio file has not completed playing in block 226, the system 100 measures the user heart rate in block 330. The system 100 calculates a difference between the measured heart rate (MHR) and the warmup heart rate (warmup HR) in block 232. In block 234, the system 100 determines whether the calculated difference is greater than a threshold value. If yes, the system 100 determines if the measured heart rate is greater than or equal to the warmup heart rate in block 236. If yes, the system 100 determines the time remaining on the currently playing audio file in block 238 (of FIG. 2D). The time remaining on the currently playing audio file is the amount of time left to play the remaining content of the currently playing audio file. For example, if a currently playing audio file has five minutes of content, and has played for three minutes, the amount of time left to play the remaining content of the currently playing audio file is two minutes.

Figure 2D:
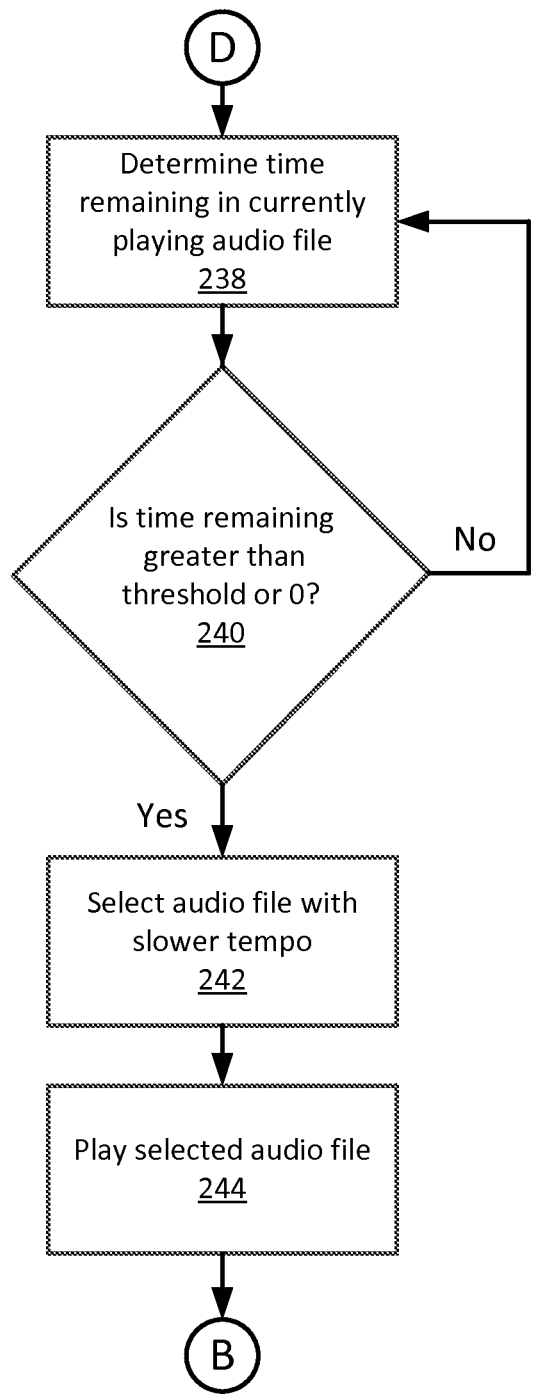

Referring to FIG. 2D, the system 100 determines in block 240 whether the time remaining in the currently playing audio file is greater than a threshold time or zero. If yes, in block 242, the system 100 selects or adjusts the tempo of the audio file to output audio to the user at a slower tempo in block 242. In block 244, the system 100 plays the selected or adjusted audio file in block 244. The determination of whether the time remaining in the audio file is greater than a threshold time or zero in block 240 allows audio files that are close to completion to finish prior to selecting and playing a new audio file. This provides a more enjoyable listening experience for the user.

Figure 2E:
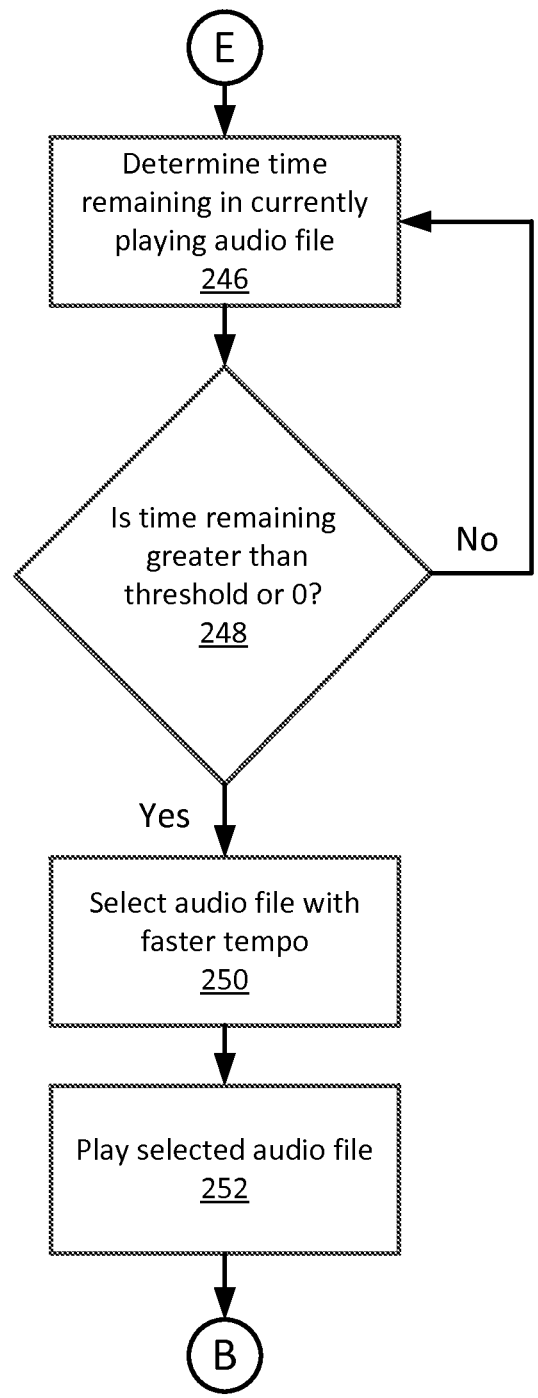

Referring to FIG. 2C, if the measured heart rate is not greater than the warmup heart rate in block 236, the system 100 determines the time remaining in the currently playing audio file in block 246 (of FIG. 2E). Referring to FIG. 2E, in block 248, the system 100 determines whether the time remaining in the playing audio file is greater than a threshold time or zero. If yes, the system 100 selects an audio file with a faster tempo in block 250 or adjusts the tempo of an audio file to have a faster tempo in block 250. In block 525, the system 100 plays the selected audio file.

Figure 2F:
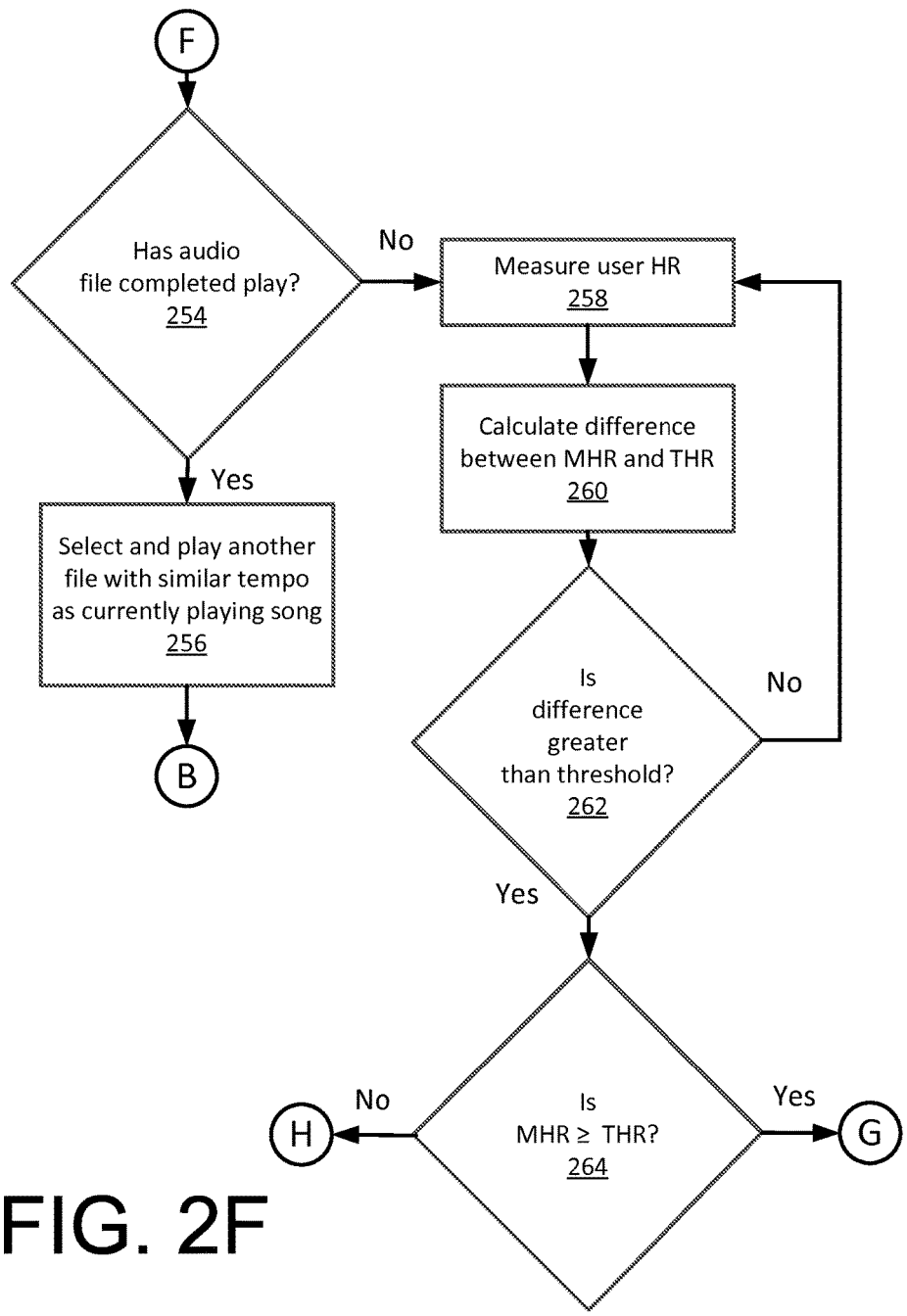

Referring to FIG. 2A, in block 212, if the warmup timer has expired in block 212, the system 100 determines whether the audio file has completed play in block 254 (of FIG. 2F). When the warmup timer expires, the warmup period has ended, and the system 100 will begin to play audio files with tempos that should bring the heart rate of the user closer to the target heart rate. Referring to FIG. 2F, if the audio file has completed play in block 252, the system 100 selects and plays another audio file with a similar tempo as the currently playing audio file in block 256.

Figure 2G:
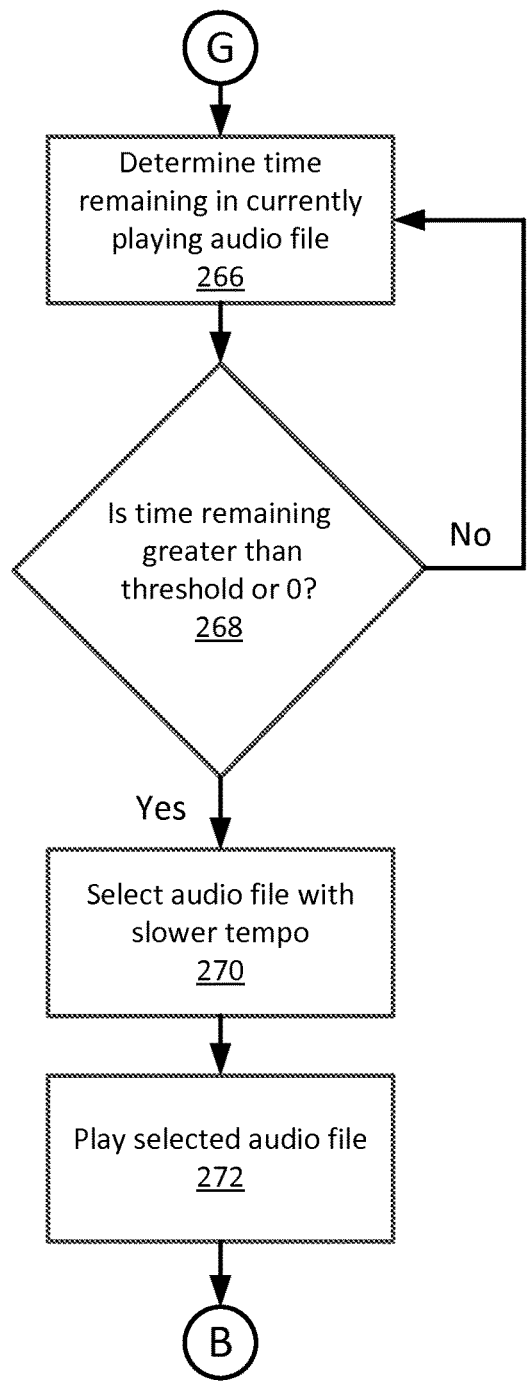

If the audio file has not completed playing in block 254, the system 100 measures the user heart rate in block 258. In block 260, the system 100 calculates the difference between the measured heart rate and the target heart rate. If the difference between the measured heart rate and the target heart rate is greater than a threshold value in block 262, the system 100 determines if the measured heart rate is greater than or equal to the target heart rate in block 264. If yes, in block 266 (of FIG. 2G), the system 100 determines the time remaining in the currently playing audio file. Referring to FIG. 2G, if the time remaining is greater than a time threshold or zero, the system 100 selects an audio file with a slower tempo in block 270 or adjusts the tempo of an audio file to a slower tempo. In block 272, the system 100 plays the selected audio file.

Figure 2H:
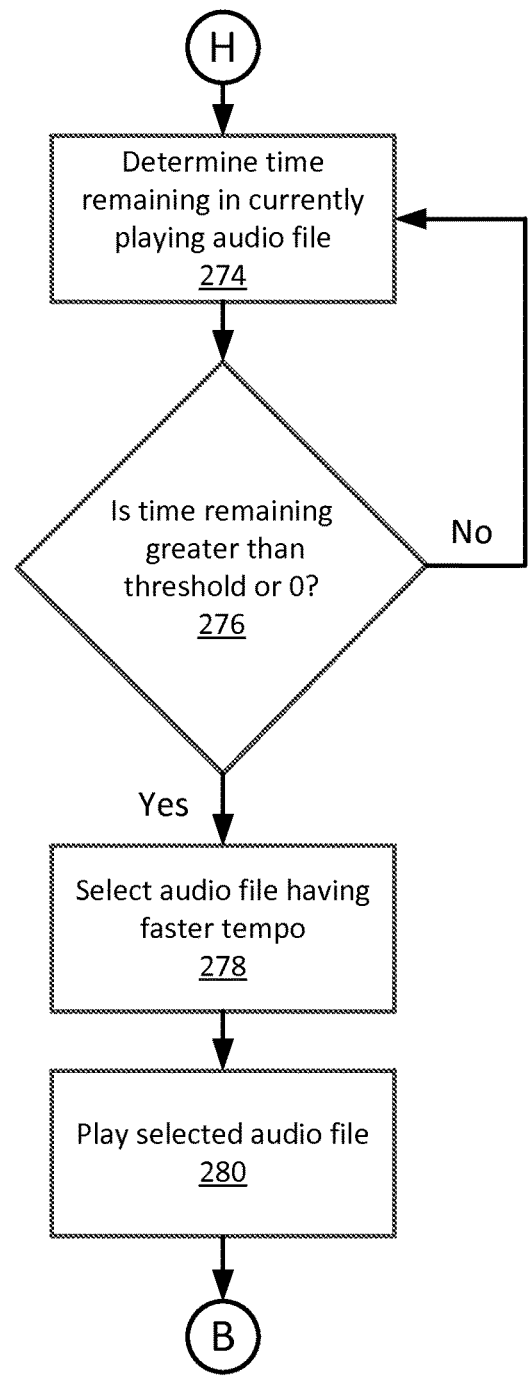

Referring to FIG. 2F, if the measured heart rate is not greater than or equal to the target heart rate in block 264, the system determines the time remaining in the currently playing audio file in block 274 (of FIG. 2H). Referring to FIG. 2H, in block 276, the system 100 determines whether the time remaining in the currently playing audio file is greater than a time threshold or zero. If yes, in block 278, the system 100 selects an audio file with a faster tempo or adjusts the tempo of an audio file to a faster tempo. In block 280, the system 100 plays the selected audio file.

The system 100 described above monitors the heart rate of a user and compares the heart rate of the user to a target heart rate. The system 100 plays audio with a tempo that is faster or slower depending on whether the user should increase or decrease their heart rate to change their heart rate to become closer to the target heart rate. Thus, the user may listen to an audio file and match the pace of their workout to the tempo of the audio file to maintain the target heart rate.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for controlling an audio output, the method comprising:
   receiving a target heart rate for a user;
   calculating a warmup heart rate for the user based at least in part on the target heart rate;

starting a warmup timer;
playing a first audio file having a first tempo, wherein the first tempo corresponds to the warmup heart rate;
determining whether the warmup timer has expired;
responsive to determining that the warmup timer has not expired,
  measuring a first heart rate of the user,
  determining whether the first heart rate of the user is greater than the warmup heart rate, and
  responsive to determining that the first heart rate of the user is greater than the warmup heart rate, playing a second audio file having a second tempo, the second tempo being slower than the first tempo; and
responsive to determining that the warmup timer has expired,
  playing a third audio file having a third tempo, wherein the third tempo corresponds to the target heart rate,
  measuring a second heart rate of a user,
  determining whether the second heart rate of the user is greater than the target heart rate,
  determining a time remaining in the third audio file,
  playing a fourth audio file having a fourth tempo, the fourth tempo being slower than the third tempo, responsive to determining that the second heart rate of the user is greater than the target heart rate and responsive to the time remaining in the third audio file being greater than a threshold,
  completing the playing the third audio file before playing the fourth audio file, responsive to the time remaining in the third audio file being less than the threshold;
  determining whether an acceleration of the user is below an acceleration threshold, and
  responsive to determining that the acceleration of the user is below the acceleration threshold, pausing the playing the third audio file or pausing the playing the fourth audio file.

2. The method of claim 1, further comprising playing a fifth audio file having a fifth tempo, the fifth tempo being faster than the third tempo, responsive to determining that the second heart rate of the user is not greater than the target heart rate.

3. The method of claim 1, further comprising:
after playing the third audio file having the third tempo, determining whether the user is moving;
pausing the play of the third audio file and starting a timer responsive to determining that the user is not moving;
determining whether the timer has expired and whether the user has resumed moving; and
resuming playing the third audio file having the third tempo responsive to determining that the user has resumed moving and that the timer has not expired.

4. The method of claim 1, wherein the first audio file includes music having the first tempo.

5. A system for outputting audio comprising:
a processor operative to:
  receive a target heart rate for a user
  calculate a warmup heart rate for the user based at least in part on the target heart rate;
  start a warmup timer;
  play a first audio file having a first tempo, wherein the first tempo corresponds to the warmup heart rate;
  determine whether the warmup timer has expired;
  responsive to determining that the warmup timer has not expired,
    measure a first heart rate of the user,
    determine whether the first heart rate of the user is greater than the warmup heart rate, and
    responsive to determining that the first heart rate of the user is greater than the warmup heart rate, play a second audio file having a second tempo, the second tempo being slower than the first tempo; and
  responsive to determining that the warmup timer has expired,
    play a third audio file having a third tempo, wherein the third tempo corresponds to the target heart rate,
    measure a second heart rate of a user,
    determine whether the second heart rate of the user is greater than the target heart rate,
    determine a time remaining in the third audio file,
    play a fourth audio file having a fourth tempo, the fourth tempo being slower than the third tempo, responsive to determining that the second heart rate of the user is greater than the target heart rate and responsive to the time remaining in the third audio file being greater than a threshold,
    completing the playing the third audio file before playing the fourth audio file, responsive to the time remaining in the third audio file being less than the threshold;
    determine whether an acceleration of the user is below an acceleration threshold, and
    responsive to determining that the acceleration of the user is below the acceleration threshold, pause the playing the third audio file or pausing the playing the fourth audio file.

6. The system of claim 5, wherein the processor is further operative to play a fifth audio file having a fifth tempo, the fifth tempo being faster than the third tempo, responsive to determining that the second heart rate of the user is not greater than the target heart rate.

7. The system of claim 5, wherein the processor is further operative to:
after playing the third audio file having the third tempo, determine whether the user is moving;
pause the play of the third audio file and starting a timer responsive to determining that the user is not moving;
determine whether the timer has expired and whether the user has resumed moving; and
resume playing the third audio file having the third tempo responsive to determining that the user has resumed moving and that the timer has not expired.

8. The system of claim 5, further comprising a heart rate monitor.

9. A computer program product for outputting audio, the computer program product comprising a non-transitory computer readable storage medium having program instructions embodied therewith, the program instructions executable by a processor to cause the processor to perform a method comprising:
receiving a target heart rate for a user;
calculating a warmup heart rate for the user based at least in part on the target heart rate;
starting a warmup timer;
playing a first audio file having a first tempo, wherein the first tempo corresponds to the warmup heart rate;
determining whether the warmup timer has expired;
responsive to determining that the warmup timer has not expired,
  measuring a first heart rate of the user, determining whether the first heart rate of the user is greater than the warmup heart rate, and responsive to determining that the first heart rate of the user is greater than the warmup heart rate, playing a second audio file having a second tempo, the second tempo being slower than the first tempo; and responsive to determining that the warmup timer has expired, playing third audio file having a third tempo, wherein the third tempo corresponds to the target heart rate, measuring a second heart rate of a user, determining whether the second heart rate of the user is greater than the target heart rate, determining a time remaining in the third audio file, playing a fourth audio file having a fourth tempo, the fourth tempo being slower than the third tempo, responsive to determining that the second heart rate of the user is greater than the target heart rate and responsive to the time remaining in the third audio file being greater than a threshold, completing the playing the third audio file before playing the fourth audio file, responsive to the time remaining in the third audio file being less than the threshold;

determining whether an acceleration of the user is below an acceleration threshold, and responsive to determining that the acceleration of the user is below the acceleration threshold, pausing the playing the third audio file or pausing the playing the fourth audio file.

10. The computer program product of claim 9, the method further comprising further comprising playing a fifth audio file having a fifth tempo, the fifth tempo being faster than the third tempo, responsive to determining that the second heart rate of the user is not greater than the target heart rate.

11. The computer program product of claim 9, the method further comprising:

after playing the third audio file having the third tempo, determining whether the user is moving;

pausing the play of the third audio file and starting a timer responsive to determining that the user is not moving;

determining whether the timer has expired and whether the user has resumed moving; and resuming playing the third audio file having the third tempo responsive to determining that the user has resumed moving and that the timer has not expired.

12. The method of claim 1, wherein calculating the warmup heart rate comprises reducing the target heart rate by a percentage.

* * * * *